US008475778B2

(12) United States Patent
Van Nguyen et al.

(10) Patent No.: US 8,475,778 B2
(45) Date of Patent: *Jul. 2, 2013

(54) AQUEOUS POLYAMINE-CONTAINING ANTI-FRIZZ COMPOSITION FOR HAIR

(75) Inventors: Nghi Van Nguyen, Edison, NJ (US); Sawa Hashimoto, Westfield, NJ (US); David W. Cannell, Plainfield, NJ (US)

(73) Assignee: L'Oreal, Paris (FR)

( * ) Notice: Subject to any disclaimer, the term of this patent is extended or adjusted under 35 U.S.C. 154(b) by 708 days.

This patent is subject to a terminal disclaimer.

(21) Appl. No.: 11/544,484

(22) Filed: Oct. 6, 2006

(65) Prior Publication Data

US 2008/0085253 A1    Apr. 10, 2008

(51) Int. Cl.
*A61K 8/89* (2006.01)

(52) U.S. Cl.
USPC ........................................................ 424/70.12

(58) Field of Classification Search
None
See application file for complete search history.

(56) References Cited

U.S. PATENT DOCUMENTS

| | | | |
|---|---|---|---|
| 3,689,424 A | | 9/1972 | Berg et al. |
| 3,790,664 A | * | 2/1974 | Krochock et al. ............... 424/47 |
| 3,883,356 A | | 5/1975 | Syrovatka et al. |
| 3,997,659 A | | 12/1976 | Knohl et al. |
| 4,275,055 A | | 6/1981 | Nachtigal et al. |
| 4,488,564 A | | 12/1984 | Grollier et al. |
| 4,663,158 A | * | 5/1987 | Wolfram et al. ............ 424/70.16 |
| 5,070,171 A | | 12/1991 | O'Lenick, Jr. |
| 5,093,452 A | | 3/1992 | O'Lenick, Jr. |
| 5,149,765 A | | 9/1992 | O'Lenick, Jr. |
| 5,196,188 A | | 3/1993 | Potthoff-Karl et al. |
| 5,248,783 A | | 9/1993 | O'Lenick |
| 5,306,484 A | | 4/1994 | Potthoff-Karl et al. |
| 5,360,581 A | | 11/1994 | Rizvi et al. |
| 5,362,484 A | * | 11/1994 | Wood et al. ............... 424/70.122 |
| 5,739,371 A | | 4/1998 | O'Lenick, Jr. |
| 5,891,956 A | | 4/1999 | Smith et al. |
| 5,897,870 A | | 4/1999 | Schehlmann et al. |
| 5,951,718 A | | 9/1999 | Krutak et al. |
| 6,139,853 A | | 10/2000 | Akram et al. |
| 6,410,005 B1 | | 6/2002 | Galleguillos et al. |
| 6,468,515 B1 | | 10/2002 | Uchiyama et al. |
| 6,540,791 B1 | | 4/2003 | Dias |
| 6,548,051 B2 | | 4/2003 | Garnier et al. |
| 6,579,846 B1 | | 6/2003 | Zirnstein et al. |
| 6,589,517 B1 | | 7/2003 | McKelvey et al. |
| 6,740,130 B2 | | 5/2004 | Sander et al. |
| 7,083,655 B2 | | 8/2006 | Pratt et al. |
| 7,094,262 B2 | | 8/2006 | Lagrange |
| 7,122,062 B2 | | 10/2006 | Yamashita et al. |
| 7,141,079 B2 | | 11/2006 | Audousset |
| 2002/0034489 A1 | | 3/2002 | Wiegland et al. |
| 2002/0064541 A1 | * | 5/2002 | Lapidot et al. ................ 424/401 |
| 2002/0143063 A1 | * | 10/2002 | Alvarado ...................... 514/642 |
| 2002/0177535 A1 | | 11/2002 | Piterski et al. |
| 2003/0108504 A1 | | 6/2003 | Sako et al. |
| 2004/0076961 A1 | | 4/2004 | Lewis |
| 2004/0120919 A1 | * | 6/2004 | Nguyen et al. ............. 424/70.16 |
| 2004/0234471 A1 | | 11/2004 | Corbella et al. |
| 2006/0008437 A1 | * | 1/2006 | Robinson et al. ............ 424/70.1 |
| 2006/0024255 A1 | | 2/2006 | Quadir et al. |
| 2006/0045862 A1 | | 3/2006 | Tada et al. |
| 2006/0286056 A1 | * | 12/2006 | Cannell et al. ............. 424/70.12 |
| 2006/0286057 A1 | | 12/2006 | Cannell et al. |
| 2009/0070945 A1 | | 3/2009 | Nguyen et al. |
| 2009/0071493 A1 | | 3/2009 | Nguyen et al. |
| 2009/0071494 A1 | | 3/2009 | Nguyen et al. |
| 2009/0071495 A1 | | 3/2009 | Nguyen et al. |
| 2009/0074700 A1 | | 3/2009 | Nguyen et al. |

FOREIGN PATENT DOCUMENTS

| | | | |
|---|---|---|---|
| EP | 1402881 | * | 3/2004 |
| WO | WO-9745510 A1 | | 12/1997 |
| WO | WO-0122928 A1 | | 4/2001 |

OTHER PUBLICATIONS

Basildon Chemicals, Product Information, BC 2366 Amodimethicone Emulsion, Mar. 2005.
Jancowicz. Conditioning Agents for Hair and Skin. Editors: Randy Schueller, Perry Romanowki. Copyrighted in 1999.
International Search Report and Written Opinion of International Application No. PCT/US2008/075851 dated Nov. 19, 2008.
CTFA Cosmetic Ingredient Handbook, First Edition, Published by the Cosmetic, Toiletry and Fragrance Association, Inc., 1110 Vermont Avenue, N.W., Washington, DC 20005, pp. 41-42, 1986.
McCutcheon's "Detergents and Emulsifiers," North American Edition (1986), published by Allured Publishing Corporation, McCutcheon Division, MC Publishing Co., 175 Rock Road, Glen Rock, NJ 07452 USA.
McCutcheon's "Functional Materials," North American Edition (1992), McCutcheon Division, MC Publishing Co., 175 Rock Road, Glen Rock, NJ 07452 USA.

* cited by examiner

*Primary Examiner* — Blessing Fubara
*Assistant Examiner* — Jennifer Berrios
(74) *Attorney, Agent, or Firm* — Novak Druce Connolly Bove + Quigg LLP

(57) ABSTRACT

The present invention is drawn to a composition and process for inhibiting hair from becoming frizzy when exposed to high and/or low humidity, the composition containing: (a) at least one fatty quaternary amine; (b) at least one nonionic surfactant; (c) at least one anionic silicone; (d) at least one water-insoluble material; (e) at least one cationic polymer; and (f) at least one film former, different from (e).

21 Claims, No Drawings

AQUEOUS POLYAMINE-CONTAINING ANTI-FRIZZ COMPOSITION FOR HAIR

STATEMENT OF RELATED APPLICATIONS

Not applicable.

BACKGROUND OF THE INVENTION

Hair fibers, depending on whether they are exposed to low or highly humid conditions, have a tendency to lose their shape, curl definition and/or become frizzy. These problems are the result of water loss or absorption from the fibers. In an effort to solve such problems, hair benefit agents such as cationic polymers are oftentimes incorporated into rinse-off hair products (shampoos, conditioners and the like) in order to seal in moisture within the hair fibers, thereby inhibiting water loss or absorption therefrom. Unfortunately, these hair benefit agents are rinsed off after their application onto the hair fibers.

It is therefore an object of the present invention to provide a composition and process for inhibiting water loss or absorption from hair fibers upon exposure to high or low humidity.

BRIEF SUMMARY OF THE INVENTION

The present invention is directed to a hair treatment composition capable of inhibiting water loss or absorption from hair fibers upon exposure to both high and low humidity can be prepared by combining:
(a) at least one fatty quaternary amine compound;
(b) at least one nonionic surfactant;
(c) at least one anionic silicone;
(d) at least one water-insoluble material;
(e) at least one cationic polymer; and
(f) optionally, at least one film former, different from (e).

In another embodiment, the present invention is also drawn to a process for inhibiting water loss or absorption from hair fibers upon exposure to both high and low humidity by contacting the hair fibers with the above-disclosed composition.

It has been surprisingly found that a hair treatment composition in accordance with the present invention, due to its ability to carry oils and deliver them to hair, enables the hair to retain water when exposed to low humidity, and inhibit water absorption when exposed to high humidity. The oils serve as a barrier, inhibiting water from escaping from, or entering into, the hair. Also, because the oils have a tendency to plate out over the surface of the hair, the cationic polymers are able to adhere more efficiently onto the hair, thereby reducing the likelihood of their being rinsed off of the hair during the shampooing process. These two phenomena enable the hair to inhibit frizz and retain curl definition at high humidity, while at the same time impart conditioning benefits onto the hair in order to protect it from becoming dry and rough at low humidity.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The term "water-insoluble" means those compounds which are either completely or partially insoluble in water.

"Amino groups" as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Ethylene oxide group" as defined herein refers to a group of formula —$CH_2CH_2$—O—.

"Propylene oxide group" as defined herein includes groups of formula —$CH_2CH_2CH_2$—O—, groups of formula ($CH_3$)$CHCH_2$—O—, and groups of formula —$CH_2$ ($CH_3$)CH—O—.

"Keratinous substrate" as defined herein may be human keratinous fiber, and may be chosen from, for example, hair, eyelashes, and eyebrows, as well as the stratum corneum of the skin and nails.

"Polymers," as defined herein, include homopolymers and copolymers formed from at least two different types of monomers.

The present invention provides for the use of conventional fatty quaternary amine compounds containing from about 6 to about 22 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, benzyl or short chain alkyl or hydroxyalkyl groups such as methyl, ethyl, hydroxymethyl or hydroxyethyl, hydroxypropyl or combinations thereof.

Examples of fatty quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowdimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowdimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, behentrimonium methosulfate (18-MEA), stearalkonium chloride, and mixtures thereof. Other quaternary ammonium compounds are listed in the CTFA Cosmetic Ingredient Handbook, First Edition, on pages 41-42, incorporated herein by reference.

In the present invention, the at least one fatty quaternary amine compound is preferably used in an amount of from greater than 0% to about 30% by weight, preferably from greater than 0% to about 10% by weight, and more preferably from greater than 0% to about 5% by weight, based on the weight of the composition as a whole.

In general, nonionic surfactants having a Hydrophilic-Lipophilic Balance (HLB) of from 8 to 20, are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated nonionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed hereinabove.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$ to $C_{30}$ alcohols, with sugar or starch polymers. These compounds can be represented by the formula $(S)_n$—O—R wherein S is a sugar moiety such as glucose, fructose, mannose, galactose, and the like; n is an integer of from about 1 to about 1000, and R is a $C_8$ to $C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$ to $C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83, Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from about 10-25, more preferably from about 10-20 moles.

The nonionic surfactant will typically be present in the composition in an amount of from greater than 0 to about 70% by weight, preferably from greater than 0 to about 40% by weight, and more preferably from greater than 0 to about 20% by weight, based on the weight of the composition as a whole.

In general, non-limiting examples of anionic silicones which may be used in the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

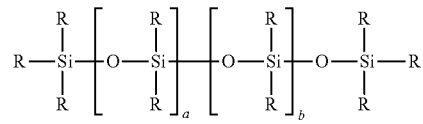

(I)

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

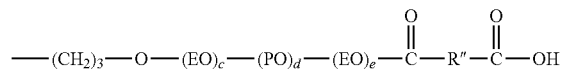

(II)

wherein: c, d, and e, which may be identical or different, are each integers ranging from 0 to 20; EO is an ethylene oxide group; PO is a propylene oxide group; and R" is chosen from optionally substituted divalent hydrocarbons, such as alkylene groups and alkenylene groups comprising from 2 to 22 carbon atoms, and optionally substituted divalent aromatic groups, such as groups of formula (III):

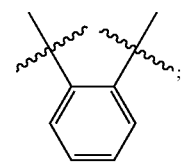

(III)

and groups of formula (IV):

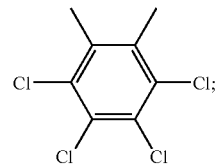

(IV)

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

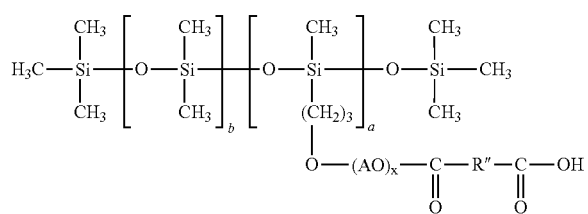

(V)

wherein: a is an integer ranging from 1 to 100; b is an integer ranging from 0 to 500; AO is chosen from groups of formula (VI):

1.  (VI)

wherein: c, d, and e, which may be identical or different, are each integers ranging from 0 to 20; EO is an ethylene oxide group; and PO is a propylene oxide group; x is an integer ranging from 0 to 60; R″ is chosen from optionally substituted divalent hydrocarbons, such as alkylene groups and alkenylene groups comprising from 2 to 22 carbon atoms, and optionally substituted divalent aromatic groups, such as groups of formula (III):

2.

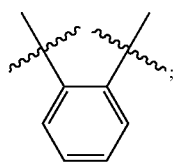

(III)

and groups of formula (IV):

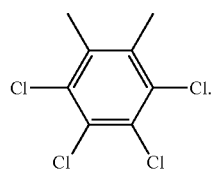

(IV)

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—$CH_2$—$CH_2$—O) and propylene oxide groups ("PO"=$C_3H_6O$).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (I):

(I)

wherein $R^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (II) and salts thereof:

(II)

wherein: c, and d, which may be identical or different, are each integers ranging from 0 to 20; e is an integer ranging from 0 to 19; and x is an integer ranging from 0 to 21; groups of formula (III) and salts thereof:

HO-(EO)$_c$—(PO)$_d$-(EO)$_e$—(CH$_2$)$_x$— (III)

wherein: c, d, and e, which may be identical or different, are each integers ranging from 0 to 20; and x is an integer ranging from 0 to 21; and groups of formula (IV) and salts thereof:

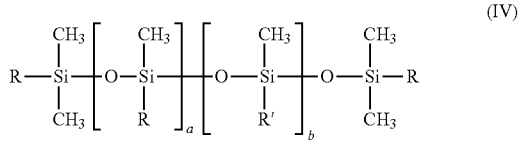

(IV)

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (III) as defined above and salts thereof, and groups of formula (V):

wherein:
the $(CH_2)_3$ end is bonded to the silicon of the compound of formula (IV) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (V) and salts thereof; and with the further proviso that at least one $R^1$ is chosen from groups of formula (IV) and salts thereof and at least one other $R^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula VI:

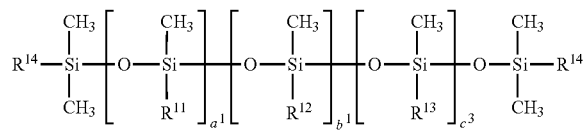

wherein $R^{11}$ is selected from lower alkyl having one to eight carbon atoms or phenyl, $R^{12}$ is $-(CH_2)_3-O-(EO)_x-(PO)_y-(EO)_z-SO_3^{31}-M^+$ wherein M is a cation and is selected from Na, K, Li, or $NH_4$; x, y and z are integers independently ranging from 0 to 100; $R^{13}$ is $-(CH_2)_3-O-(EO)_x-(PO)_y-(EO)_z-H$; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula VII:

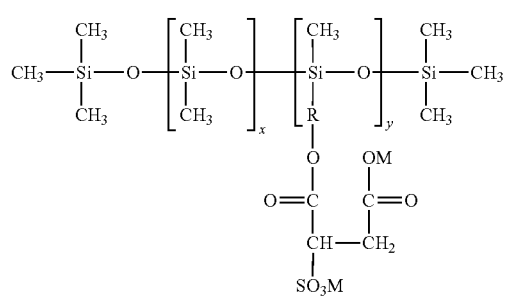

wherein R represents a divalent radical selected from

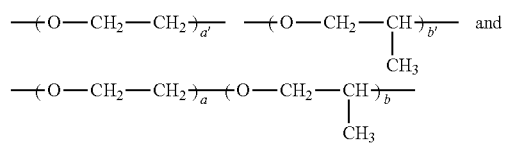

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the tradename Ultrasil PE-100.

The anionic silicone is present in the composition in an amount ranging from greater than 0 to about 50% by weight, preferably from greater than 0 to about 30% by weight, and more preferably from greater than 0 to about 15% by weight, based on the weight of the composition as a whole.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

The cationic polymer is generally present in an amount of from greater than 0% to about 15%, preferably from about 0.5 to about 10% by weight, and more preferably from about 1 to about 5% by weight, based on the total weight of the composition.

Film forming polymers useful herein are neutralized or partially neutralized polymers and resins such as, for example, those containing carboxyl moieties, such as acrylates and other carboxy polymers. Examples of suitable water soluble film forming polymers include, for example, PVP, PVP/VA, acrylates, polyesters, polyurethranes, polyimides, polysulfonates, guars, starches and the like. Typically, water-insoluble polymers and resins have to be neutralized to about 90% of their carboxyl moieties to make them water soluble for the purpose of formulating products in aqueous solution and for the purpose of making products which have good non-build-up properties, i.e., can be easily washed off the hair after use.

The following are examples of film forming polymers that may be used in the compositions of the present invention. The list is not intended to be limiting:

AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylate/t-butyl acrylamide),
SALCARE SC60 from Ciba (Acrylamidopropyltrimonium Chloride/Acrylamide Copolymer),
BALANCE CR from National Starch (Acrylates Copolymer),
AMPHOMER 28-4961 from National Starch (Acrylates/Octylacrylamide Copolymer),
TORAY SETSIL 301 from Dow Corning (Acrylates/Octylacrylamide/Diphenyl Amodimethicone Copolymer),
DIAFORMER Z-632N from Clariant (Acrylates/Stearyl Acrylate/Ethylamine Oxide Methacrylate Copolymer),
ULTRAHOL 8 from BASF (Acrylates/t-Butylacrylamide Copolymer),
MEXOMERE PQ from Chimex (Allyl Stearate/VA Copolymer),
FIXATE G-100 from Noveon (AMP-Acrylates/Allyl Methacrylate Copolymer),
GANTREZ A-425 from ISP (Butyl Ester of PVM/MA Copolymer),
GANEX P-904 from ISP (Butylated PVP),
AMAZE from National Starch (Corn Starch Modified),
MEXOMERE PL from Chimex (Diethylene Glycolamine/Epichlorohydrin/piperazine Copolymer),
EASTMAN AQ POLYMER from Eastman (Diglycol/CHDM/Isophthalate/SIP Copolymer),
JAGUAR C 13S from Rhodia (Guar Hydroxylpropyl Trimonium Chloride),
AQUAFLEX FX-64 from ISP (Isobutylene/Ethylmaleimide/Hydroxyethylmaleimide Copolymer),
LUVIFLEX SILK from BASF (PEG/PPG-25/25 Dimethicone/Acrylates Copolymer),
AQUAFLEX XL-30 from BASF (Polyimide-1),
LUVISET P.U.R from BASF (Polyurethrane-1),
LUVISKOL PLUS from BASF (Polyvinylcaprolactam),
AQUAFLEX SF-40 from ISP (PVP/Vinylcaprolactam/DMAPA Acrylates Copolymers),
ADVANTAGE PLUS from ISP (VA/Butyl Maleate/Isobornyl Acrylate Copolymer),
MEXOMERE PW from Chimex (VA/Vinyl Butyl Benzoate/Crotonates Copolymer),
GAFFIX VC-713 from ISP (Vinyl Caprolactam/VP/Dimethylaminoethyl Methacrylate Copolymer),
COPOLYMER 845 from ISP (VP/Dimethylaminoethylmethacrylate Copolymer),
GANEX V-516 from ISP (VP/Hexadecene Copolymer),
LUVISKOL VA 64 from BASF (VP/VA Copolymer).

Unneutralized or partially neutralized water-insoluble latexes can also be used as invention film-forming polymers. Included are the following latexes:
AMERHOLD DR-25 from Amerchol (acrylic acid/methacrylic acid/acrylates/methacrylates),
LUVIMER 36D from BASF (ethyl acrylate/t-butyl acrylate/methacrylic acid), and
ACUDYNE 258 from Rohm & Haas (acrylic acid/methacrylic acid/acrylates/methacrylates/hydroxy ester acrylates).

The film forming polymer may be employed in an amount ranging from greater than 0 to about 15% by weight, preferably from about 0.5 to about 10% by weight, and more preferably from about 1 to about 5% by weight, based on the total weight of the composition.

Suitable water-insoluble materials or ingredients for use in the present invention include, but are not limited to, the following:

(1) Lipophilic "ingredients" or "materials" such as silicones, oil-soluble vitamins such as Vitamin E and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, aminosilicone and laurylmethicone copolyol. The lipophilic ingredients will, for example, moisturize or condition the skin, hair, and/or eyelashes and leave behind no oily feel.

(2) Water-insoluble polymers, resins, and latexes, wherein the polymers and resins include but are not limited to those containing carboxyl moieties, such as acrylates and other carboxy polymers.

Preferred water-insoluble ingredients for use in the present invention include silicones ranging from low molecular weight fluids to high molecular weight gums; hydrocarbons such as mineral oil, petrolatum, paraffins, iso-paraffins, aromatic hydrocarbons, and the like; plant oils such as olive, avocado, coconut, and the like; fatty acids; fatty esters; fatty alcohols; and fatty waxes.

The water-insoluble material may be employed in an amount ranging from greater than 0 to about 30% by weight, preferably from about 0 to about 15% by weight, and more preferably from about 0 to about 5% by weight, based on the total weight of the composition.

Auxiliary Ingredients

Suitable small molecules for use in the present invention are those having the ability to both penetrate keratin fibers and help prevent and/or slow down water loss therefrom. Examples thereof include, but are not limited to, polar amino acids and their salts/derivatives, urea and its salts/derivatives, guanidine and its salts/derivatives, and combinations thereof.

Polar amino acids may be chosen from arginine, asparagine, aspartic acid (or aspartate), glutamine, glutamic acid (or glutamate), histidine, lysine, serine, and threonine. These amino acids are hydrophilic due to their polar side chains. Lysine and arginine are positively charged at neutral pH, whereas histidine can be uncharged or positively charged depending on its local environment.

Alternatively, proteins, polypeptides or other natural extracts having a high polar amino acid content can be used. For example, proteins having a major proportion of arginine units (in the range from about 50 to about 90%, by weight, of the total protein) in their structures are members of that class of proteins known as protamines. The protamine proteins are characterised by having: (a) a low molecular weight, in the range of about 5,000; (b) a high isoelectric point, in the pH range of about 10 to 12; and (c) a high arginine content, in the range from about 50 to about 90%, by weight of the total protein.

Proteins of high polar amino acid content as described above can be subjected to acid or base hydrolysis to yield polypeptides which also have a high polar amino acid content. Examples of suitable polypeptides are also described in U.S. Pat. No. 3,997,659, being protamine-derived polypeptides having a molecular weight below about 5,000, a basic pH (10-12), and an arginine content of about 50%, or greater, by weight of the total polypeptide.

Not only may naturally occurring proteins be used, but also synthetic proteins, for example, polylysine and polyarginine, or mixtures thereof.

An example of a suitable natural extract which is rich in arginine is aloe vera extract.

The polar amino acids and the proteins and polypeptides having a polar amino acid content of 50%, or greater, are often isolated from natural sources in the form of salts and hydrosalts, which are also suitable for use according to the invention. Such salts and hydrosalts are formed by reaction with mineral acids such as hydrochloric acid, phosphoric acid, carbonic acid, sulfuric acid, nitric acid, and the like, or the organic acids such as formic acid, acetic acid, lauric acid, chloroacetic acid and the like. A suitable example is arginine hydrochloride.

Preferred small molecules for use in the present invention are arginine and urea, as well as their respective salts and/or hydrosalts.

The amount of small molecules which may be employed in the present invention will range from greater than 0 to 10% by weight, preferably from 0.01 to 5% by weight, and more preferably from 0.1 to 1% by weight, based on total weight of the composition.

The composition of the present invention preferably has a pH ranging from 2-12, preferably from 4 to 10, and more preferably from 5 to 8.

The present invention is also directed to a process for inhibiting hair fibers from losing water, in general, and especially when exposed to low or high humidity. The process involves contacting the hair fibers with the above-described composition.

The present invention will be better understood by the examples which follow, all of which are intended for illustrative purposes only, and are not meant to unduly limit the scope of the invention in any way.

EXAMPLE

The following example is intended for illustrative purposes only, and is not meant to unduly limit the scope of the invention in any way. This example illustrates the necessity of a shampoo containing a fatty quaternary amine, a nonionic surfactant, an anionic silicone (act as a carrier of a water insoluble material) to have both the cationic polymer and the film former to show good anti-frizz properties and better curl definition.

The following formulas I-IV were made:

| Phase | | I | II | III | IV |
|---|---|---|---|---|---|
| A | Deionized Water | 41.05% | 62.55% | 42.75% | 64.25% |
| A | AMP | 0.20% | 0.20% | — | — |
| A | Amphomer LV-71 | 1.50% | 1.50% | — | — |
| B | Deionized Water | 10.00% | 10.00% | 10.00% | 10.00% |
| B | Behentrimonium Chloride | 0.20% | 0.20% | 0.20% | 0.20% |
| B | Ultrasil PE-100 | 0.40% | 0.40% | 0.40% | 0.40% |
| B | Procetyl AWS | 6.00% | 6.00% | 6.00% | 6.00% |
| B | Olive Oil | 0.30% | 0.30% | 0.30% | 0.30% |
| C | Deionized Water | 20.00% | — | 20.00% | — |
| C | Polymer JR-30 | 1.50% | — | 1.50% | — |
| D | SLES-2 (Sodium Laureth-2 Sulfate) (70% conc.) | 13.85% | 13.85% | 13.85% | 13.85% |
| D | Cocamidopropyl Betaine | 5.00% | 5.00% | 5.00% | 5.00% |

All of the formulas I-IV above are clear formulas.

Procedure to make formulas I-IV: In beaker A, add amount of phase A water and heat to 85° C. with moderate mixing. Add AMP and Amphomer LV-71, if necessary, with high speed mixing. Mix well until uniform and clear. In beaker B, add amount of phase B water and heat to 85° C. with moderate mixing. At 85° C., add Behentrimonium Chloride, Ultrasil PE-100, Procetyl AWS, and Olive oil, with high speed mixing. Mix well until uniform and clear. Next, add contents of beaker A into beaker B. Mix well and maintain at 85° C. until uniform. If necessary, in beaker C, add amount of phase C water and with high speed mixing, sift in polymer JR-30. Mix well until it gels up. Add beaker C contents into phase A and B mixture above. Mix well until uniform. Start cooling batch to RT. Reduce mixer speed to moderate speed and add SLES-2 and Cocamidopropyl Betaine. Gently mix to prevent aeration and cool to RT.

The above formulas I-IV were used to assess anti-frizz properties using the anti-frizz test method as described as follows: Hair swatches of 0.3 g and 18 cm long each were shampooed with 0.5 g of product for 15 seconds, then rinsed out after 1 minute for 10 seconds. These swatches were wound onto the pegboards to create two dimensional wave patterns, and placed in 50° C. oven for 1 hour. After equilibrating at RT overnight, the swatches are unwound, then photocopied. T0, or initial area of the hair, was taken by tracing the perimeter of the photocopied swatch and calculating the area of the hair using an image analysis software. These swatches are hung in the humidity chamber (RH 90-95%) for 4 hours. After 4 hours, or at T4, the areas are again taken by photocopying the swatches, then tracing them and calculating the areas. The % change of the area of the swatches is calculated using the following calculation: (T4−T0)/T0×100, and the final results are averaged. The formulas that prevent frizz will be indicated by lower % change. The results are as shown below:

| | Formula I | Formula II | Formula III | Formula IV |
|---|---|---|---|---|
| % change | 264% | 1443% | 474% | 1205% |

The above results show that formula III showed significant prevention of frizz when compared to formula IV. Formula I, containing all three components, also showed significant prevention of frizz compared to formula IV. However it also showed to have the best curl definition when compared to hair treated with formulas II, III, and IV.

It will be apparent to those skilled in the art that numerous modifications and variations can be made without departing from the spirit or scope of the invention.

What is claimed is:

1. A process for inhibiting hair from becoming frizzy when exposed to high and/or low humidity comprising contacting the hair with a clear composition containing:
   (a) at least one fatty quaternary amine compound, wherein the fatty group comprises about 6 to about 22 carbon atoms;
   (b) at least one nonionic surfactant;
   (c) at least one anionic silicone;
   (d) at least one oil;
   (e) at least one cationic polymer; and
   (f) at least one film former, different from (e).

2. The process of claim 1 wherein (a) is behentrimonium chloride.

3. The process of claim 1 wherein (a) is present in an amount from greater than 0 to about 30% by weight, based on the weight of the composition.

4. The process of claim 1 wherein (a) is present in an amount from greater than 0 to about 5% by weight, based on the weight of the composition.

5. The process of claim 1 wherein (b) has an HLB of at least 8.

6. The process of claim 1 wherein (b) is present in an amount from greater than 0 to about 70% by weight, based on the weight of the composition.

7. The process of claim 1 wherein (b) is present in an amount from greater than 0 to about 20% by weight, based on the weight of the composition.

8. The process of claim 1 wherein (c) is a silicone phosphate.

9. The process of claim 1 wherein (c) is a silicone carboxylate.

10. The process of claim 1 wherein (c) is a silicone sulfate.

11. The process of claim 1 wherein (c) is present in an amount from greater than 0% to about 50% by weight, based on the weight of the composition.

12. The process of claim 1 wherein (c) is present in an amount from greater than 0 to about 15% by weight, based on the weight of the composition.

13. The process of claim 1 wherein (d) is present in an amount from greater than 0 to about 30% by weight, based on the weight of the composition.

14. The process of claim 1 wherein (d) is present in an amount from greater than 0 to about 5% by weight, based on the weight of the composition.

15. The process of claim 1 wherein (e) is present in an amount from greater than 0 to about 15% by weight, based on the weight of the composition.

16. The process of claim 1 wherein (e) is present in an amount from about 1 to about 5% by weight, based on the weight of the composition.

17. The process of claim 1 wherein (f) is present in an amount from greater than 0 to about 15% by weight, based on the weight of the composition.

18. The process of claim 1 wherein (f) is present in an amount from about 1 to about 5% by weight, based on the weight of the composition.

19. The process of claim 1, wherein
   (a) is behentrimonium chloride and is present in an amount from greater than 0 to about 5% by weight;
   (b) has an HLB of at least 8, and is present in an amount from greater than 0 to about 20% by weight;
   (c) is selected from the group consisting of a silicone phosphate, a silicone carboxylate, and a silicone sulfate, and is present in an amount from greater than 0 to about 15% by weight;
   (d) is present in an amount from greater than 0 to about 5% by weight; and
   (e) is present in an amount from about 1 to about 5% by weight; and
   (f) is present in an amount from about 1 to about 5% by weight. based on the total weight of the composition.

20. The process of claim 19, wherein (c) comprises dimethicone.

21. the process of claim 20, wherein (c) is dimethicone PEG-8 phosphate.

* * * * *